United States Patent [19]

McCarthy

[11] 4,188,824
[45] Feb. 19, 1980

[54] COATING ADHERENCE PROSPENSITY TESTING OF METAL SUBSTRATES

[75] Inventor: Edward P. McCarthy, Lansing, Ill.

[73] Assignee: Youngstown Sheet and Tube Company, Pittsburgh, Pa.

[21] Appl. No.: 911,936

[22] Filed: Jun. 2, 1978

[51] Int. Cl.² .......................................... G01N 17/00
[52] U.S. Cl. .................................... 73/150 A; 73/1 R
[58] Field of Search ............... 73/150 R, 150 A, 1 R, 73/432 R; 23/253 C; 148/6.15 R, 6.15 Z

[56] References Cited

U.S. PATENT DOCUMENTS 3,899,364  8/1975  Evans ............................. 148/6.15 R
4,000,012  12/1976  Burrows ......................... 148/6.15 R

*Primary Examiner*—S. Clement Swisher
*Assistant Examiner*—Denis E. Corr
*Attorney, Agent, or Firm*—John Stelmah

[57] ABSTRACT

A method for testing a treated metal substrate toward its propensity to receive and adherently retain a finish coat such as paint or the like; the test is made before the finish coat is applied by applying a strip of adhesive to a specimen treated substrate, stripping the tape, and then comparing the amount of "soil" pick-up versus an established standard; "soil" includes any of the treating material picked up by the tape from the treated substrate.

9 Claims, 19 Drawing Figures

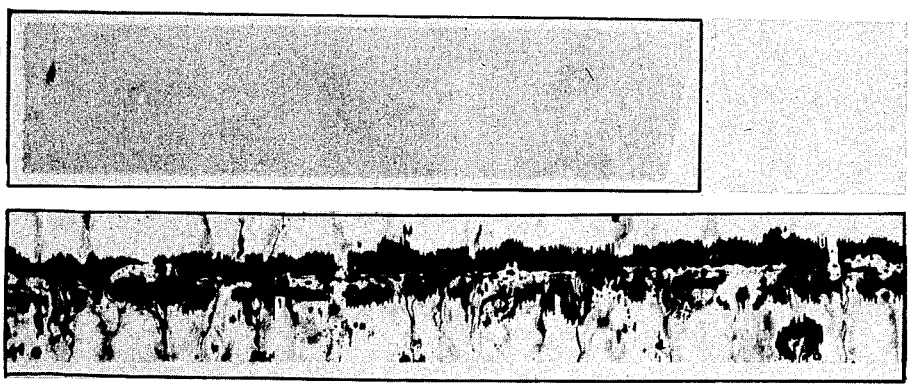
FIG.6C FIG.6B FIG.6A
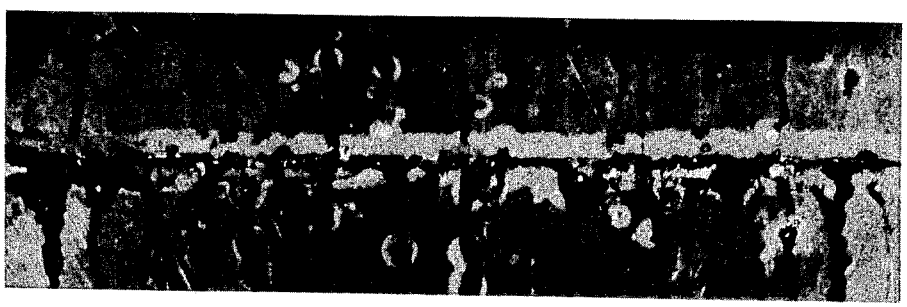
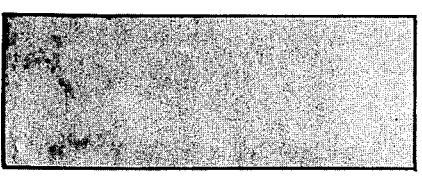
FIG.5C
FIG.5B
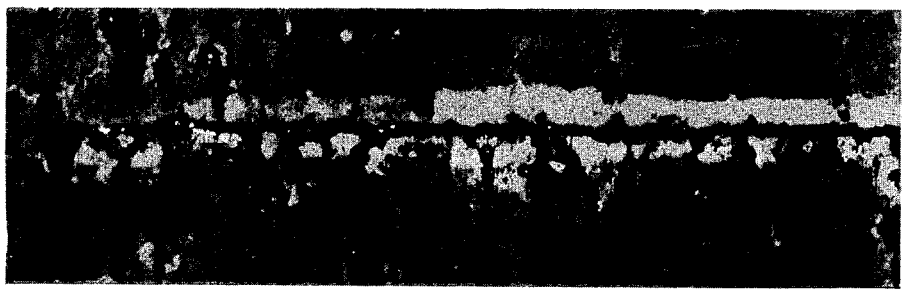
FIG.5A

COATING ADHERENCE PROSPENSITY TESTING OF METAL SUBSTRATES

BACKGROUND OF THE INVENTION AND DESCRIPTION OF PRIOR ART

In the automotive and appliance industries it is generally known to apply chemical bond coatings to parts fabricated of metal prior to applying a finish coat. Chemical bond coatings, such as phosphates, on metals are used to promote adhesion of finish coats, such as paint, varnish lacquer, and the like, to the substrate. Such phosphate coating additionally provides some underpaint corrosion protection. The chemical bond coatings are usually applied to individual component parts after fabrication from stock material, e.g., sheet steel, but in some cases such coatings may be applied to sub or complete assemblies. The components are frequently coated at the end of an assembly line prior to assembly and painting.

It is known in the art of coating metal substrates to first apply a chemical bonding coat, apply a film of paint or the like over the chemical bonding coat, and then to test the adherence of the paint film. The most generally accepted testing procedure involves the ASTM method designated as B117 Salt Spray Testing. Contingent upon a particular user's requirements the B117 testing method takes over 100 hours and may take as many as 336 hours to complete.

A problem which has plagued the art of painting metal substrates is that of finding a suitable and satisfactory technique for testing and assessing the propensity of a metal substrate to receive and adherently retain a paint film, i.e., before the paint is applied.

In the art of coating steel substrates it is known to use phosphates as a chemical bonding coat for a finish paint coat. Most phosphate coating quality control methods are based on visual inspections and until recently most of the industry has assumed that if a uniform and completely covering phosphate coating was present on the steel substrate the outer paint film would inherently adhere. Accordingly, previous testing procedures were provided for measuring the concentration of the phosphate coating, such as that disclosed in U.S. Pat. No. 3,899,364, or else for evaluating the integrity of the coating, such as that disclosed in *Metals Handbook*, 8th edition, Vol. 2, published by American Society for Metals, Metals Park, Ohio, page 544. The procedure described in the *Metals Handbook* involves the use of a special solution containing potassium ferricyanide and sodium chloride; a chromotography filter paper is dipped into the solution and placed on the surface to be evaluated; after five minutes the test paper is lifted and the phosphate exposed surface is inspected for blue color; the quality of phosphate covering is rated in accordance with the absence of or amount of blue color, with the most desirable result being no blue color.

While such integrity test is effective toward assessing whether a full coat has been applied to the substrate it is not effective toward assessing the "bite" or adherence of the coating with the substrate. It is this adherence with which the present invention is primarily concerned. The testing procedure of this invention provides a method through which the results of more time consuming paint film adhesion tests can be anticipated with a high degree of reliability. Such time consuming tests include those as described in U.S. Pat. Nos. 3,899,364 and 4,000,012 where the specimen panels are tested after the paint films are applied. U.S. Pat. No. 4,000,012 also discloses a presently accepted technique in the automotive industry for evaluating the adherence of paint on a steel substrate. This technique involves the above referred to ASTM method B117 Salt Spray Testing.

OBJECTS AND SUMMARY OF THE INVENTION

An object of the present invention is to provide a method for assessing the suitability of a metal substrate to receive and adherently retain a coating film. Another object is to provide a method for anticipating the adherence behavior of a chemically treated metal substrate. A further object is to provide a method whereby the results of paint film adhesion tests for metal substrates can be reliably predicted and in a relatively short time. A specific object is to provide a method for evaluating the adherence of a coating chemically reactive with a metal substrate. A more specific object is to provide a method for predicting and evaluating the adherence behavior of a film of paint with a phosphated steel substrate.

Briefly, according to the present invention there is provided a method for evaluating the suitability of a metal substrate, such as steel, which has been treated with a chemical reaction coat, i.e., one which reacts with the metal to form therewith a substantially insoluble salt, e.g., zinc-phosphate, which comprises applying to a representative test specimen a strip of pressure sensitive transparent tape, peeling the tape from the substrate, observing and comparing the quantity and type of soil removed with the tape from the substrate ("soil" as used herein includes any contaminants as well as any of the coating which is removed by the tape from the substrate) with characterizing base standards. Additionally, the peeled tape may be placed on a light colored background material and a photocopy made to facilitate the making of the comparison and also to provide a file record of the test. The making of the comparison is facilitated because the appearance of any soil will be manifested as dark spots or areas against the light colored background.

BRIEF DESCRIPTION OF THE PHOTOGRAPHS

The accompanying photographs are based upon actual specimens prepared and tested in accordance with the method of this invention and with the ASTM Salt Spray Test B117. The photographs are printed on sensitized paper in lieu of India ink drawings to illustrate results which are believed to be incapable of being accurately or adequately depicted in India ink drawings.

FIGS. 1A–6A are photographs of six separate steel panel specimens which are phosphate treated, painted, scored to break the paint film, and then subjected to the ASTM Salt Spray Test B117 for 240 hours;

FIGS. 1B–6B are photographs of tapes applied to panel specimens shown in FIGS. 1A–6A, respectively, after being subjected to salt spray as part of the paint film adhesion evaluation;

FIGS. 1C–6C are photographs of tapes applied to panel specimens shown in FIGS. 1A–6A, respectively, after the panels were phosphate treated but before being painted; the tapes were applied within one inch of the scribe line areas.

Figures 2B, 2C, 7:
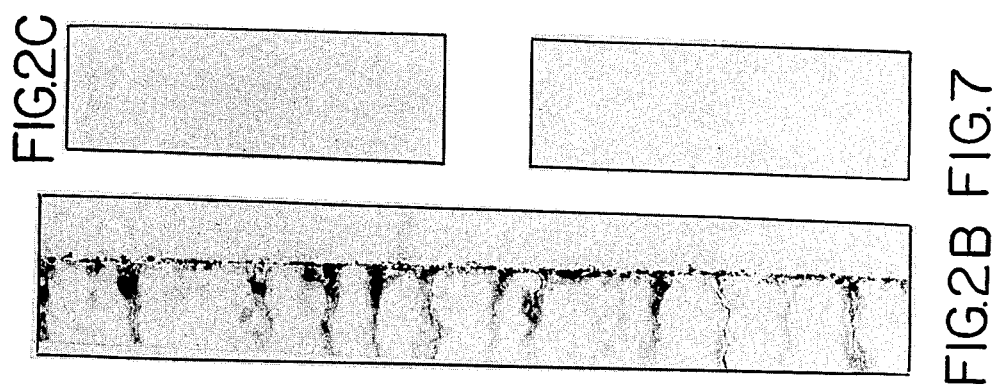
FIG. 7 is a photograph of a clear clean tape applied against a plain light paper background; the tape being of the type as applied in FIGS. 1C–6C.
Figure 2A:

The tapes together with their attached paper backgrounds shown in FIGS. 1B–6B, 1C–6C, and 7 are outlined in India ink to enchance their delineations.

DETAILED DESCRIPTION

The process of this invention is particularly adapted for use in conjunction with duplex coating systems which employ phosphates as chemical undercoats, such as those used in the automotive industry, and hence preferred embodiments will be described in that connection. However, it will be understood that the process may be used in conjunction with other primer coats or undercoats. It will be understood that "test specimens" as used herein includes the material used in or on the production of commercial products as well as separate representative samples of the material contemplated to be used in the commercial products.

A common method for phosphate coating of metal parts or substrates, prior to painting, generally comprises six steps: (1) cleaning; (2) pre-phosphating rinsing; (3) phosphating; (4) post-rinsing; (5) acidic sealing rinse, such as chromic acid treating; and (6) rinsing. It is understood, however, that some of these steps may be omitted and/or that steps may be added, depending upon the type of material to be coated and on the surface condition of the material.

The cleaning step (1) may involve chemical or mechanical actions and is conducted in order to facilitate uniform wetting of the substrate surface with the phosphating solution, otherwise, any soil on the substrate might act as a barrier to the phosphating.

The pre-phosphating rinsing step (2) usually involves the application of hot water, by spray or immersion, to remove any of the cleaning agent of step (1) that might adhere to the surface.

The application (3) of the phosphating solution is usually by spraying but can be by immersion. The solution may be of the zinc, iron, or manganese types. It is important that the operating temperature be controlled since too low a temperature will produce a thin or no coating whereas too high a temperature will produce an excess build-up with a non-adherent powdery surface.

The post-phosphating step (4) rinsing with running water is employed to remove any active chemicals that remain on the surface and which might contaminate the acidic seal of step (5). The water should not be so hot as to set the chemicals.

The acidic sealing rinse of step (5) is used to seal any of the phosphating acid that might remain on the substrate surface, to improve resistance to salt spray corrosion, and to reduce paint film blistering. Chromic acids and fluorides have been found to be suitable for these purposes.

The parts are removed from the solution of step (5), rinsed with running water, Step 6, and dried.

The parts are subsequently painted and specimens are selected for the salt spray testing. Lines are then scored across the selected specimens to break the paint film. The panels are then subjected to continuous salt spray in accordance with ASTM B117 procedures for a number of hours selected by the processer to suit the particular requirements of the end use of the parts.

As will be apparent, the generally employed salt spray test is an after-the-fact test, i.e., it does not test or provide a way to predict the suitability of a treated substrate to receive and maintain adherence of subsequent coatings, but rather is a test to ascertain whether good adherence does exist between an applied finish coating and the substrate. A failure in the salt spray test might be attributed to any one or more of several causes such as (a) substrate surface soil; (b) poor phosphating practice, including any of the preparation procedures; and (c) poor painting or curing practices.

In contradistinction, the present invention provides a testing procedure whereby any of the potential causes for failure may be pin-pointed by applying a test at any of the stages or steps in the procedure which may be questionable, e.g., after the initial cleaning or pre-rinsing steps. The present invention also recognizes that poor phosphating practice and adherence may be a cause of poor paint or other finish coating adherence even though the phosphate coating may uniformly cover the substrate or base material.

An important role of the present invention is the provision of an intermediate test, i.e., after the production of the phosphate coating and before the application of the paint film, which intermediate test provides means for assessing the tenacity of the phosphate coating with the substrate. As far as is known, no one has provided, prior to this invention, a procedure for evaluating the tenacity of a chemical reactive coating with a metal substrate, nor a procedure whereby the adherence or a subsequently applied paint film can be predicted.

The test of this invention comprises the steps of applying a strip of adhesive tape to the treated substrate, or a representative sample thereof, prior to application of the decorative or finish coating, pressing the tape firmly unto the substrate, peeling the tape with a quick and steady motion, and characterizing the soil on the tape in relation to acceptable standards (previously derived) toward providing a suitable substrate for receiving a coating.

The amount of material (soil) removed from a substrate surface by its respective tape strip is used as the criterion for assessing the propensity of the treated surface to receive and retain a further finish coating or film, such as plastic, paint, or the like; an increased amount of soil adhering to the tape indicates a decrease in the propensity for good adherence of the finish coat. In a preferred embodiment of the invention a transparent pressure sensitive tape (such as Scotch brand No. 600 or equivalent) is used and the peeled tape is pressed unto a light colored background material (white paper) in order to provide maximum contrast with any soils or contaminants peeled from the substrate with the tape.

Figures 1B, 1C:
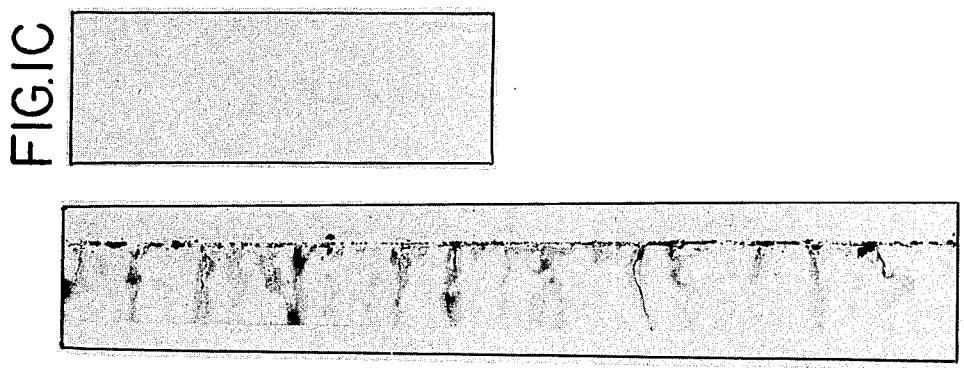
Figure 1A:
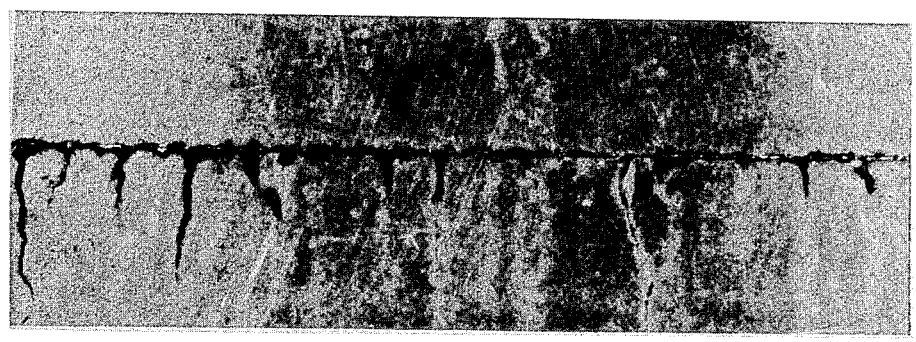
Figure 4C:
Figure 4B:
Figure 4A:
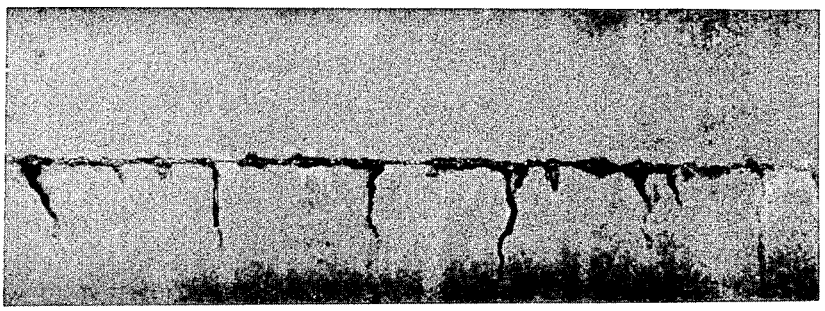
Figure 3C:
Figure 3B:
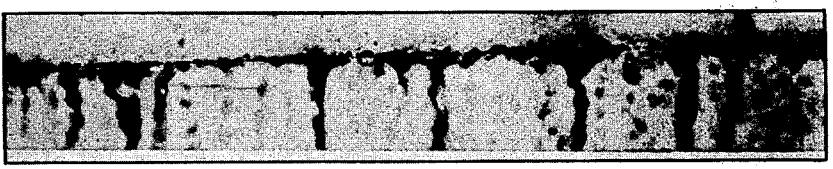
Figure 3A:
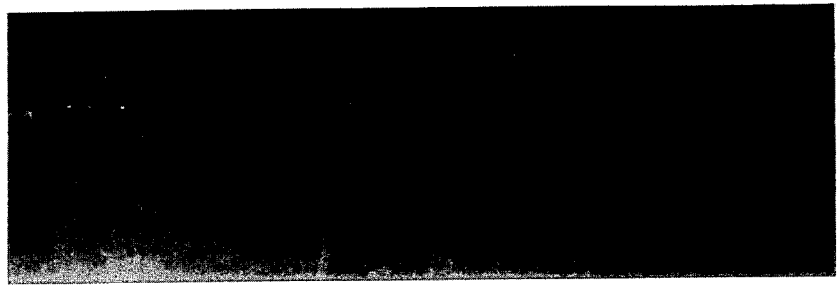

In the photographs the results of testing six panels are shown. The photographs of the tests relating to the same panel are designated by the same numeral; however, the different stages or tests are further designated by a different letter suffix, i.e., FIG. 1A is a photograph of panel No. 1 after being subjected to a phosphate treatment corresponding to the common method described heretofore, after being painted, and after being subjected to the ASTM Salt Spray B117 for 240 hours, and to which a strip of transparent tape has been applied along the score line and stripped; FIG. 1B is a photograph of the transparent tape strip applied to panel No. 1, after the salt spray test, and after being stripped from the panel; whereas, FIG. 1C is a photograph of the transparent tape (on a white paper background) placed on panel No. 1 after the panel was phosphate treated but before painting, the tape having been applied to the panel in an area about one inch away from where the scribe line was subsequently scored.

The photographs designated as FIGS. 2B–6B and FIGS. 2C–6C correspond in like manner to panels 2–6, respectively.

In FIGS. 1C and 2C it will be observed there is very little pick-up of soil by the tapes applied to panels 1 and 2. This indicates that panels 1 and 2 should have excellent propensities for receiving and retaining paint films. The prediction of the excellent adherent propensities is borne out by the results of the salt spray tests shown in FIGS. 1A and 2A, where it will be observed there is very little rusting outside of the score line and virtually no peeling of the paint away from the score line. The characteristic of excellent adherence is also manifested by the minute amount of paint pick-up shown on tapes of FIGS. 1B and 2B. Thus, the tapes shown in FIGS. 1C and 2C could be used as standards for future tests for assessing future tapes which correspond thereto, in the amount of soil pick-up, as predictions of good finish coat adherence and as having correlation with the acceptable standards of the ASTM Salt Spray Test B117.

In FIGS. 5C and 6C it can be observed there is a substantial amount of pick-up of soil by the tapes applied to panels 5 and 6 that the paint adherence after the salt spray tests would be poor. The predictions were proven to be accurate by the results shown in FIGS. 5A and 6A where the panel specimens display substantial degrees of paint peeling and rusting at or near the score lines. Thus, the tapes shown in FIGS. 5C and 6C could be used as standards in future tests for assessing correspondingly soiled treated substrates as being clearly unacceptable for painting since they indicate poor adherence of the base undercoat and for correlation with the standards of the ASTM Salt Spray Test B117.

As implied from the above descriptions of the processing and testing of panels 1, 2, 5, and 6, the test tapes shown in FIGS. 1C and 2C indicate that the steel and processing through the phosphating step used in connection with specimen panels 1 and 2 should provide substrates having excellent propensities for receiving and adhering a film of paint, and the test tapes shown in FIGS. 5C and 6C indicate that the steel or processing through the phosphating step used in connection with specimen panels 5 and 6 will result in substrates having poor paint film propensities. These results might be considered to be representative of the extreme ends of the standards for assessing acceptable and unacceptable substrates prior to finish coating. There exists a large "grey" area between the "white" and "black" poles of acceptance and unacceptance within which area many of the substrates might be classified: Panels 3 and 4 might be considered by some to be within such grey area. In this particular case they were considered to be acceptable. However, since the processing materials and procedures may vary from one metal fabricator to the next, it will be apparent that a fixed comparison base standard may not prove to be satisfactory to all. Each fabricator or user of chemically treated substrates such as described here, or the like, should ascertain his own standards to be used for comparison. The tapes shown in FIGS. 3C and 4C might depict such a standard, i.e., any tape strip compared therewith containing the same amount or less soil might be considered acceptable, and any tape strip compared therewith containing more soil might be considered unacceptable.

The present invention provides a facile, quick and inexpensive technique for testing and assessing the condition and suitability of a metal substrate, before the substrate is formed into commercial production items, toward receiving and adherently maintaining a finish coat during exposure to conditions corresponding to those in salt spray tests. In the case of steel, the testing can be conducted at the steel supplier's facilities by duplicating the pre-finish coating procedures of the steel fabricator on specimens of steel to be supplied. Hence, it the steel specimens are assessed to be unacceptable from the standpoint of finish coat adherence, much time, money, and the steel itself can be saved. (The steel can be diverted to another use.)

What is claimed is:

1. A method for testing and assessing the propensity of a metal substrate having thereon a chemical bonding base coating to receive and adherently retain a finish coat, which method comprises:
   applying a strip of pressure sensitive tape onto a completely unscribed area of the chemical bonding base coating of a test specimen of said substrate in the absence thereon of a finish coat;
   stripping said strip of tape together with any of said chemical coating which adheres thereto; and
   comparing the amount of the chemical coating and other soil adhered to said tape with an established characterizing base standard which standard is a measure of adherence about a scribing of a similar finish coat received on a similar chemical bonding base coating on a similar metal substrate.

2. The method as described in claim 1, wherein:
   said tape is of a clear transparent type, and is affixed to a light background material after being stripped from said substrate.

3. A method as described in claim 1, wherein:
   said characterizing standards are correlated with an ASTM B117 Salt Spray Test.

4. A method as described in claim 1, wherein:
   said chemical coating is of a phosphate bearing type.

5. The method as described in claim 2, which further comprises:
   making a photocopy of the stripped tape on the background material.

6. A method of testing phosphate treated steel substrates for adherence propensity, which method comprises:
   applying a strip of adhesive tape to a completely unscribed area of the phosphate of a substrate specimen to cause any unadhered phosphate and other soil on the substrate to adhere to said strip;
   peeling said strip together with any adhered soil from said substrate; and
   comparing the amount of soil adhered to said tape with an established base standard which standard is a measure of adherence propensity about a scribing of a finished coat received on a similarly phosphate treated steel substrate.

7. A method for preparing and testing the propensity of a steel specimen to have a finish coating adhere to the surface of said specimen, which process comprises the following steps in sequential order:
   (a) immerse said specimen for one minute in an alkaline cleaner solution, said solution being at a temperature of about 180° F.;
   (b) remove said specimen and, without drying, rinse in hot running water;
   (c) immerse the specimen for one minute in an activating solution for activating a phosphate solution, being at a temperature of about 160° F.;
   (d) remove said specimen and, without rinsing, immerse for about one minute in a zinc-phosphate solution, said zinc-phosphate solution being at a temperature of about 160° F.;
(e) remove said specimen and rinse in hot running water;
(f) immerse said specimen for about one minute in a chromium solution, said chromium solution being at a temperature of about 160° F.;
(g) remove said specimen and rinse in running water;
(h) air dry said specimen;
(i) apply transparent adhesive tape with firm pressure to said specimen;
(j) strip said tape from said specimen together with any unadhered phosphate and other soil; and
(k) comparing the soil removed from said specimen with an established standard.

8. The method as described in claim 7, wherein:
(l) the established standard is correlated with ASTM Salt Spray Testing.

9. The method as described in claim 7, wherein: the stripped tape of step (j) is affixed to a light colored background to facilitate the comparing of step (k).

* * * * *